United States Patent
Kostuik et al.

(10) Patent No.: US 9,579,127 B2
(45) Date of Patent: Feb. 28, 2017

(54) FIXATION IMPLANT AND METHOD OF INSERTION

(71) Applicant: K2M, Inc., Leesburg, VA (US)

(72) Inventors: John Kostuik, Baltimore, MD (US); Richard W. Woods, Catonsville, MD (US); Nick Missos, Leesburg, VA (US); Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 115 days.

(21) Appl. No.: 14/207,740

(22) Filed: Mar. 13, 2014

(65) Prior Publication Data

US 2014/0277162 A1   Sep. 18, 2014

Related U.S. Application Data

(60) Provisional application No. 61/778,588, filed on Mar. 13, 2013.

(51) Int. Cl.
   *A61B 17/70*      (2006.01)
   *A61B 17/16*      (2006.01)

(52) U.S. Cl.
   CPC ...... *A61B 17/7055* (2013.01); *A61B 17/1642* (2013.01); *A61B 17/1671* (2013.01); *A61B 17/70* (2013.01); *A61B 17/7034* (2013.01); *A61B 17/7035* (2013.01); *A61B 17/7037* (2013.01)

(58) Field of Classification Search
   CPC ............ A61B 17/1642; A61B 17/7055; A61B 17/1671; A61B 17/7034; A61B 17/7035; A61B 17/7037

USPC .................................. 606/264–272, 309–319
See application file for complete search history.

(56) References Cited

U.S. PATENT DOCUMENTS

| | | | | |
|---|---|---|---|---|
| 4,790,303 A | * | 12/1988 | Steffee | 606/300 |
| 6,086,589 A | | 7/2000 | Kuslich et al. | |
| 6,599,294 B2 | | 7/2003 | Fuss et al. | |
| 6,923,811 B1 | * | 8/2005 | Carl et al. | 623/17.11 |
| 7,909,871 B2 | | 3/2011 | Abdou | |
| 8,357,197 B2 | | 1/2013 | McGraw et al. | |
| 8,409,208 B2 | | 4/2013 | Abdou | |
| 8,641,766 B2 | * | 2/2014 | Donner et al. | 623/17.16 |

(Continued)

FOREIGN PATENT DOCUMENTS

| | | |
|---|---|---|
| NL | 1 009 471 | 12/1999 |
| WO | WO 2009/004625 | 1/2009 |

(Continued)

OTHER PUBLICATIONS

Partial European Search Report dated Jun. 24. 2014 issued in European Application No. 14159452.

(Continued)

*Primary Examiner* — Ellen C Hammond
(74) *Attorney, Agent, or Firm* — Carter, DeLuca, Farrell & Schmidt, LLP (57) ABSTRACT

An implant includes an implantable portion and a housing. The implantable portion has a head and a shank extending from the head. The shank has a solid outer surface and defines a radius of curvature. The housing is pivotally and rotatably coupled to the head and is configured to secure a rod to the implantable portion. The housing is fixed relative to the implantable portion when a rod is secured within the housing.

22 Claims, 13 Drawing Sheets

(56) References Cited

U.S. PATENT DOCUMENTS

| | | | |
|---|---|---|---|
| 2008/0039843 A1* | 2/2008 | Abdou | 606/61 |
| 2009/0187191 A1* | 7/2009 | Carl et al. | 606/80 |
| 2010/0262196 A1* | 10/2010 | Barrus et al. | 606/308 |
| 2011/0172772 A1* | 7/2011 | Abdou | 623/17.11 |
| 2012/0239090 A1* | 9/2012 | Abdou | 606/264 |
| 2012/0262196 A1 | 10/2012 | Yokou | |

FOREIGN PATENT DOCUMENTS

| | | | | |
|---|---|---|---|---|
| WO | WO 2009004625 A2 * | 1/2009 | | A61B 17/70 |
| WO | WO 2010/121028 | 10/2010 | | |
| WO | WO 2010121028 A2 * | 10/2010 | | A61B 17/70 |

OTHER PUBLICATIONS

Extended European Search Report dated Aug. 13, 2014, issued in European Application No. 14159452.

* cited by examiner

FIXATION IMPLANT AND METHOD OF INSERTION

CROSS-REFERENCE TO RELATED APPLICATIONS

The present application claims the benefit of, and priority to, U.S. Provisional Patent Application Ser. No. 61/778,588, filed on Mar. 13, 2013, the entire contents of which is incorporated herein by reference.

BACKGROUND

1. Technical Field

The present disclosure relates to methods, systems, and apparatuses for bony fixation and, more specifically, to methods, systems, and apparatuses adapted for fixing the bones of the spine.

2. Discussion of Related Art

Fixation or fusion of vertebral columns with bone or material, rods or plates is a common, long practiced surgical method for treating a variety of conditions. Many of the existing procedures involve the use of components that protrude outwardly, which may contact and damage a body part, such as the aorta, the vena cava, the sympathetic nerves, the lungs, the esophagus, the intestine, and the ureter. In addition, many constructions involve components that may loosen and cause undesirable problems, often necessitating further surgical intervention. Additionally, limiting the success of these procedures are the biomechanical features of the spine itself, whose structure must simultaneously provide support to regions of the body, protect the vertebral nervous system, and permit motion in multiple planes.

As indicated above, spinal surgery for spine fusion generally involves using implants and instrumentation to provide support to the affected area of the spine while allowing the bones thereof to fuse. The technology initially evolved using bone chips around and on top of an area of the spine that had been roughened to simulate a fracture in its consistency. The area, having encountered the bone chips, would then proceed to heal like a fracture, incorporating the bone chips.

Surgical procedures dealing with the spine present notable challenges. For example, bioengineers have been required to identify the various elements of the complex motions that the spine performs, and the components of the complex forces it bears. This complexity has made it difficult to achieve adequate stability and effective healing in surgical procedures directed to the spine. One surgical technique, involves cutting a dowel type hole with a saw across or through the moveable intervertebral disc and replacing it with a bone graft that was harvested from the hip bone. This procedure limits motion and mobility and results in a fusion of the adjacent vertebral bodies. However, as a result of the complex motions of the spine, it is often difficult to secure the dowel from displacing. Further, it has become apparent over time that this particular technique does not always yield a secure fusion.

Other techniques have been developed that involve the placement of various hardware elements, including rods and hooks, rods and screws and plates and screws. The dowel technique also has advanced over the past five years or so, with dowels being fabricated from cadaver bone or metals such as titanium or stainless steel. These techniques, whether using hardware, dowels or some combination thereof, have a common goal to enhance stability by diminishing movement, thereby resulting in or enhancing the potential of a fusion of adjacent vertebral bones. For example, in one of these other techniques, the disc is removed and adjacent vertebrae are positioned in a stable position by placing a plate against and traversing them, which plate is secured or anchored to each by means of screws.

Thus, it would be desirable to provide a new apparatus, system, and methods for spinal fixation that enhances healing of the bone while providing structural support to the spine. It would be particularly desirable to provide such an apparatus, system, and method that would involve the use of open surgical or minimally invasive surgical techniques. In addition, it would be desirable for an implant placeable adjacent the sacrum at the end of a long construct with numerous screws and/or hooks securing one or more rods to the spine where fixation at the sacrum can experience considerable stress, which can in some instances break traditional screws, pull rods free from screws or fatigue the bone-screws interface, in all cases compromising the security of the fixation to the sacrum.

SUMMARY

In an aspect of the present disclosure, an implant includes an implantable portion and a housing. The implantable portion includes a head and a shank extending from the head. The shank defines a radius of curvature and has a solid outer surface. The housing is pivotally and rotatably coupled to the head. The housing is configured to secure a rod to the implantable portion. The housing is fixed relative to the implantable portion when a rod is secured to the implantable portion.

The housing may be a taper lock housing or a set screw housing. The shank may define a plurality of recesses in the outer surface thereof. The shank may be generally cylindrical. The head and the shank may be integrally formed with one another. The shank may be a solid shaft. The outer surface of the shank may be uninterrupted.

In embodiments, the implant portion is for insertion through a sacrum of a patient and into an L5 vertebra of the patient to create a fusion of the sacrum and the L5 vertebra.

In some aspects of the present disclosure, a system for inserting an implant in bony anatomy of a patient includes an implant and a drilling apparatus. The implant may be any of the implants disclosed herein. The drilling apparatus includes a drill guide assembly and a drill shaft assembly. The drill guide assembly includes a guide shaft and a distal section. The guide shaft defines a drill channel and the distal section defines a guide slot in communication with the drill channel. The drill shaft assembly includes a proximal portion, a flexible distal portion, and a curved guide. The proximal and distal portions of the drill shaft assembly are slidably and rotatably disposed within the drill channel. The curved guide is coupled to the flexible distal portion and is slidably disposed within the guide slot. The curved guide deflects the flexible distal portion as the drill shaft assembly advances through the drill guide assembly such that the flexible distal portion defines a curved path.

The drill shaft assembly may include a drill tip coupled to a distal end of the flexible distal portion and configured to forward cut and side cut bone in contact therewith. The curved guide may include a coupling mechanism that is adjacent a first end thereof. The coupling mechanism may capture the flexible distal portion while permitting the flexible distal portion to rotate relative to the curved guide. The coupling mechanism may prevent the first end of the curved guide from sliding through the guide slot. The curved guide may include a stop adjacent a second end thereof that prevents the second end of the curved guide from sliding through the guide slot.

In certain aspects of the present disclosure, a method of fixing two bony elements relative to one another includes inserting an implant portion into a curved drilled hole defined in two bony elements of a patient and permitting bone growth of the bony elements to secure an implantable portion of the implant within the curved drilled hole to fuse the two bony elements to one another. The method may include fixing a housing relative to the implant. The method may also include securing a rod in the housing of the implant.

In embodiments, the method includes drilling the curved drilled hole in a first bony element and into a second bony element with a drilling apparatus. The drilling apparatus may be any of the drilling apparatuses disclosed herein. Drilling the curved drilled hole may include coupling a curved guide to a flexible distal portion. Drilling the curved drilled hole may include advancing the drill shaft assembly through the drill channel such that the flexible distal portion defines a curved path. Advancing the drill shaft assembly may include steering the flexible distal portion along the curved path with the curved guide. The method may further include selecting a curved guide with a radius of curvature substantially equal to a radius of curvature of the shank of the implant. The radius of curvature of the curved guide may define the curved path of the drilled hole.

The implant may burrow in the vertebral body, traverse across the disk space, and end in an adjacent or neighboring vertebrae or vertebras, to provide limited or no protrusions. The implant may be retained within the bone without requiring contour-varying external vertebral wall fixation as compared to conventional devices, as such the implant may avoid blood vessel injury or erosion into organs and may be placeable near nerves. In addition, the implant may be utilized in the sacral region of the spine to attach spinal rods typically used in a spinal constructs that run longitudinally down either side of the spinous process providing further support to the construct. Further, the implant may be placeable at the end of a long construct with numerous screws and/or hooks securing one or more rods to the spine where fixation at the sacrum can experience considerable stress.

Further, to the extent consistent, any of the aspects described herein may be used in conjunction with any or all of the other aspects described herein.

Certain embodiments of the present disclosure may include some, all, or none of the above advantages. One or more other technical advantages may be readily apparent to those skilled in the art for the figures, descriptions, and claims included herein. Moreover, while specific advantages have been enumerated above, various embodiments may include all, some, or none of the enumerated advantages.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is farthest from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1:
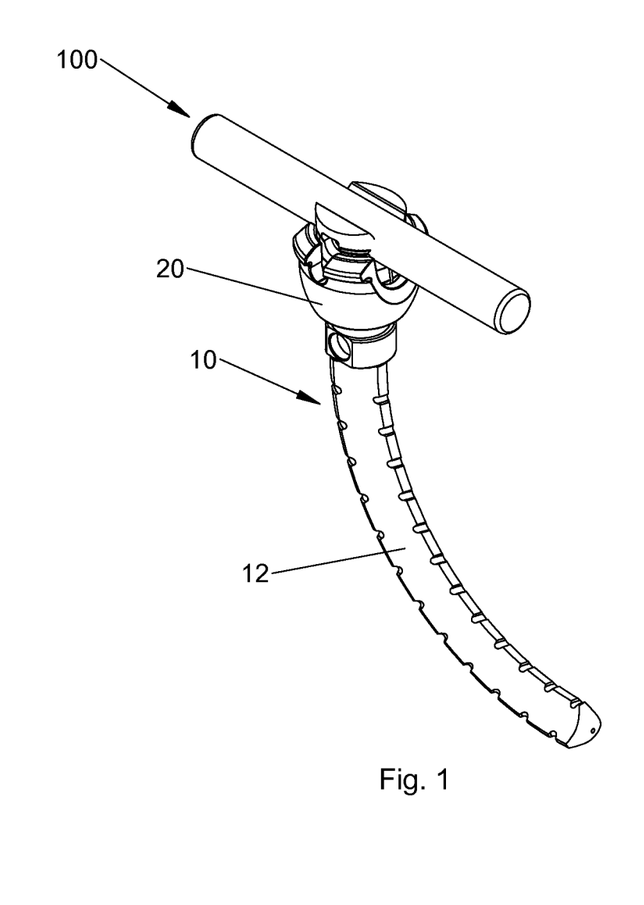
FIG. 1 is a perspective view of an implant in accordance with the present disclosure receiving a spinal rod.
Figure 2:
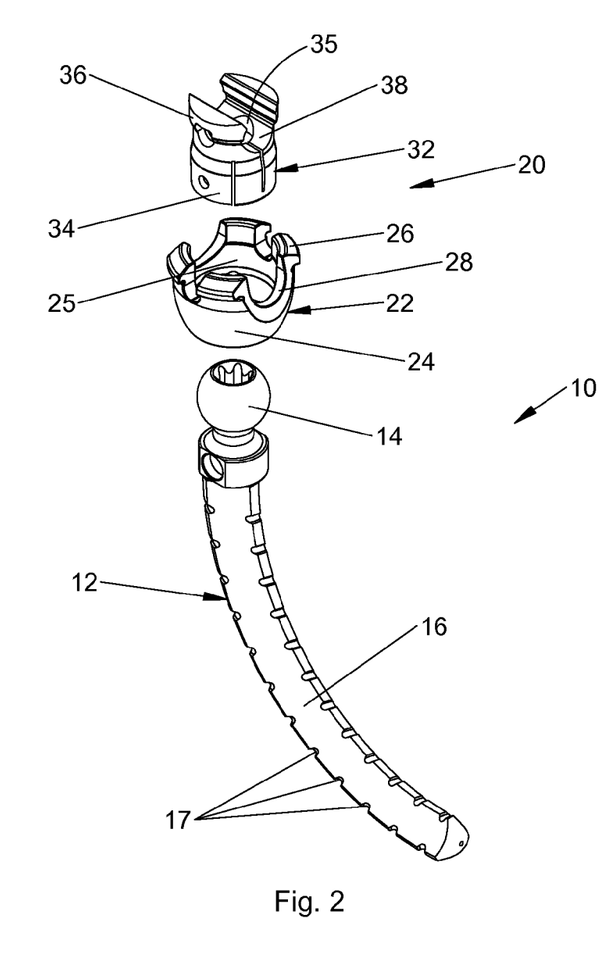
FIG. 2 is an exploded view of the implant of FIG. 1.
Figure 3:
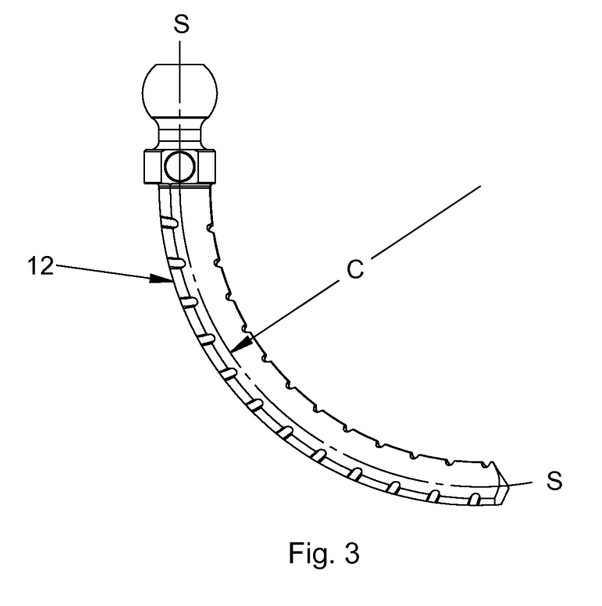
FIG. 3 is a side view of the implant portion of the implant of FIG. 1.

Referring now to FIGS. 1-3, an implant 10 is provided in accordance with the present disclosure including an implantable portion 12 and a housing 20. The implant portion 12 provides a mounting or anchoring point for a spinal rod 100. In addition, the implant portion 12 may secure two or more bony elements (e.g., a sacrum and a vertebra) together to facilitate fusion of the two or more bony elements. Portions of the implant portion 12 and the housing 20 may be made of any suitable biocompatible material including but not limited to titanium, titanium alloys, stainless steel, cobalt chrome, nickel titanium, or polymer compositions.

The implant portion 12 includes a head 14 and a shank 16 extending from the head 14. The head 14 and the shank 16 may be integrally formed with one another that may increase the strength of the overall construct or that may simplify the use of the implant portion 12 as detailed below. The shank 16 is rigid along its length. The shank 16 may have a solid outer surface that is uninterrupted along its length. In embodiments, the shank is a solid shaft. In some embodiments, the shank 16 is a solid shaft with a hollow core or channel (not shown) to reduce the weight and/or material used to manufacture the shank 16. The outer surface of the shank 16 may be non-porous. Additionally or alternatively, the outer surface of the shank 16 may include surface features to promote bone growth including, but not limited to, ridges, indentations, or textures.

The shank 16 defines a radius of curvature C. The radius of curvature C may be constant along the entire length of the shank 16. However, it is also within the scope of this disclosure that the radius of curvature of the implant portion may vary along the length of the shank 16 (e.g., the radius of curvature may increase or decrease along the length of the shank 16). The shank 16 has a substantially constant diameter along the entire length thereof. The diameter of the shank 16 may be from about 4 mm to about 12 mm (e.g., about 8 mm). It is also within the scope of this disclosure that the shank 16 is less than 4 mm or greater than 12 mm.

The shank 16 defines a plurality of recesses 17 in an outer surface thereof and defines an arcuate axis S-S. Each recess 17 may be a ring about the outer surface of the shank and substantially orthogonal to the axis S-S defined by the shank 16. It is also within the scope of this disclosure that each recess 17 is a groove helically disposed in the outer surface of the shank 16 along the axis S-S. The recesses may increase the surface area of the outer surface of the shank 16. The increased surface area of the outer surface of the shank 16 may promote bone ingrowth to the shank and/or increase the retention of the shank within a bony element of the anatomy as detailed below.

The housing 20 is pivotally mounted over the head 14 of the implant portion 12. The head 14 of the implant portion 12 is substantially spherical to permit the housing 20 to pivot or rotate about the head 14. The housing 20 is configured to secure a rod (e.g., spinal rod 100) to the implant 10. When a rod is secured within the housing 20, the housing may be pivotally or rotatably fixed relative to the implant portion 12. The housing 20 includes an outer housing or coupling 22, and an inner housing or collet 32. The coupling 22 includes an annular body portion 24 having an opening 25 extending axially therethrough. Additionally, the coupling 22 includes a plurality of fingers 26 that are located in opposing regions of the coupling 22 and define a saddle 28 having a generally U-shaped configuration. The U-shaped saddle 28 is configured and dimensioned for receiving a rod. The collet 32 has a generally cylindrical body portion 34 with an opening 35 extending axially therethrough. A pair of upstanding wings 36 defines a saddle 38 having a generally U-shaped configuration. The saddle 38 is configured and dimensioned for receiving a rod. The wings 36 compress towards each other to engage an outer surface of a rod located in the saddle 38, thereby frictionally securing the rod in a desired position relative to the implant portion 12. As detailed above, the housing 20 is configured as a taper lock housing; however, it is also within the scope of this disclosure that the housing 20 is configured as a set screw housing. An exemplary embodiment of a taper lock housing is disclosed in commonly owned U.S. patent application Ser. No. 12/739,461 filed Apr. 23, 2010, and published as U.S. Patent Pub. No. 2010/0262196, and an exemplary embodiment of a set screw housing is disclosed in commonly owned U.S. Pat. No. 7,947,066, the contents of each is incorporated herein in its entirety.

Figure 4:
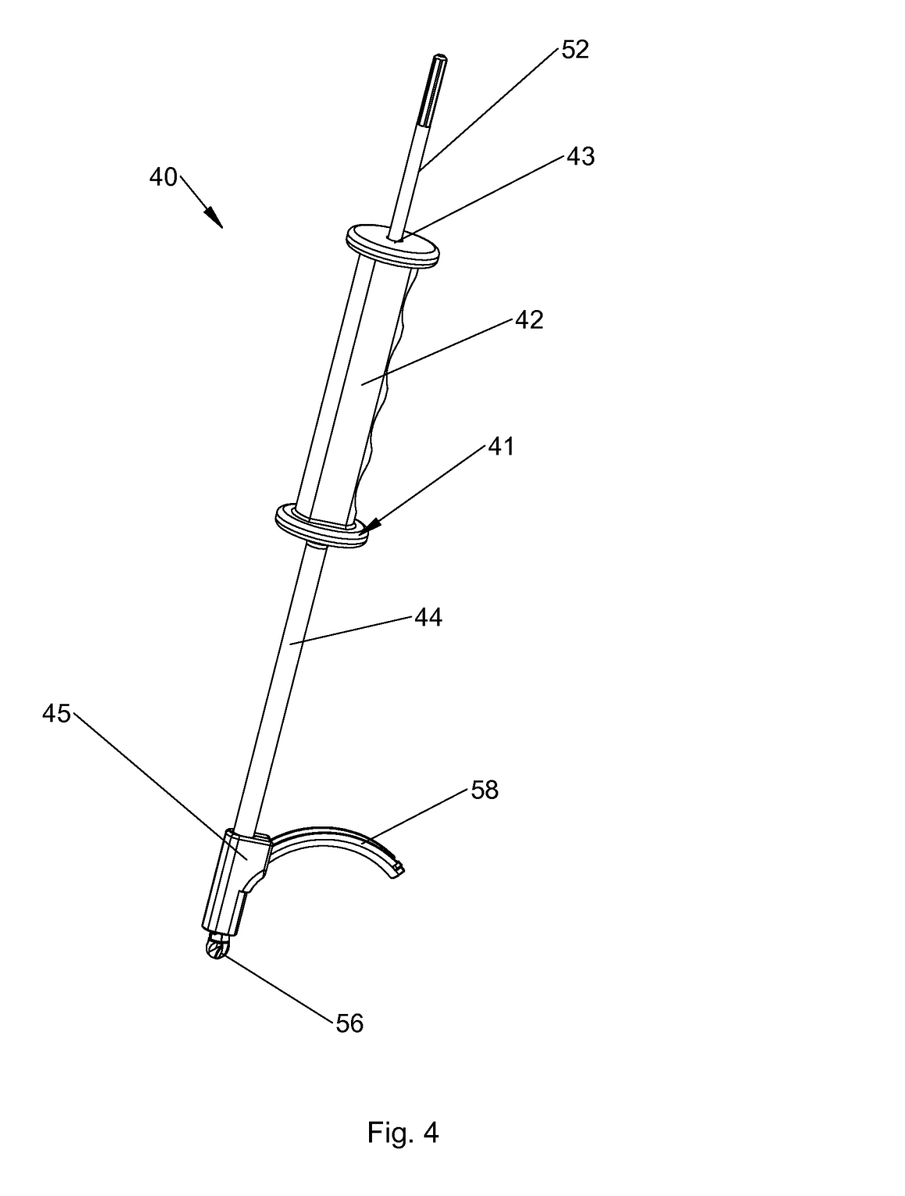
FIG. 4 is a side perspective view of a drilling apparatus in accordance with the present disclosure.
Figure 5:
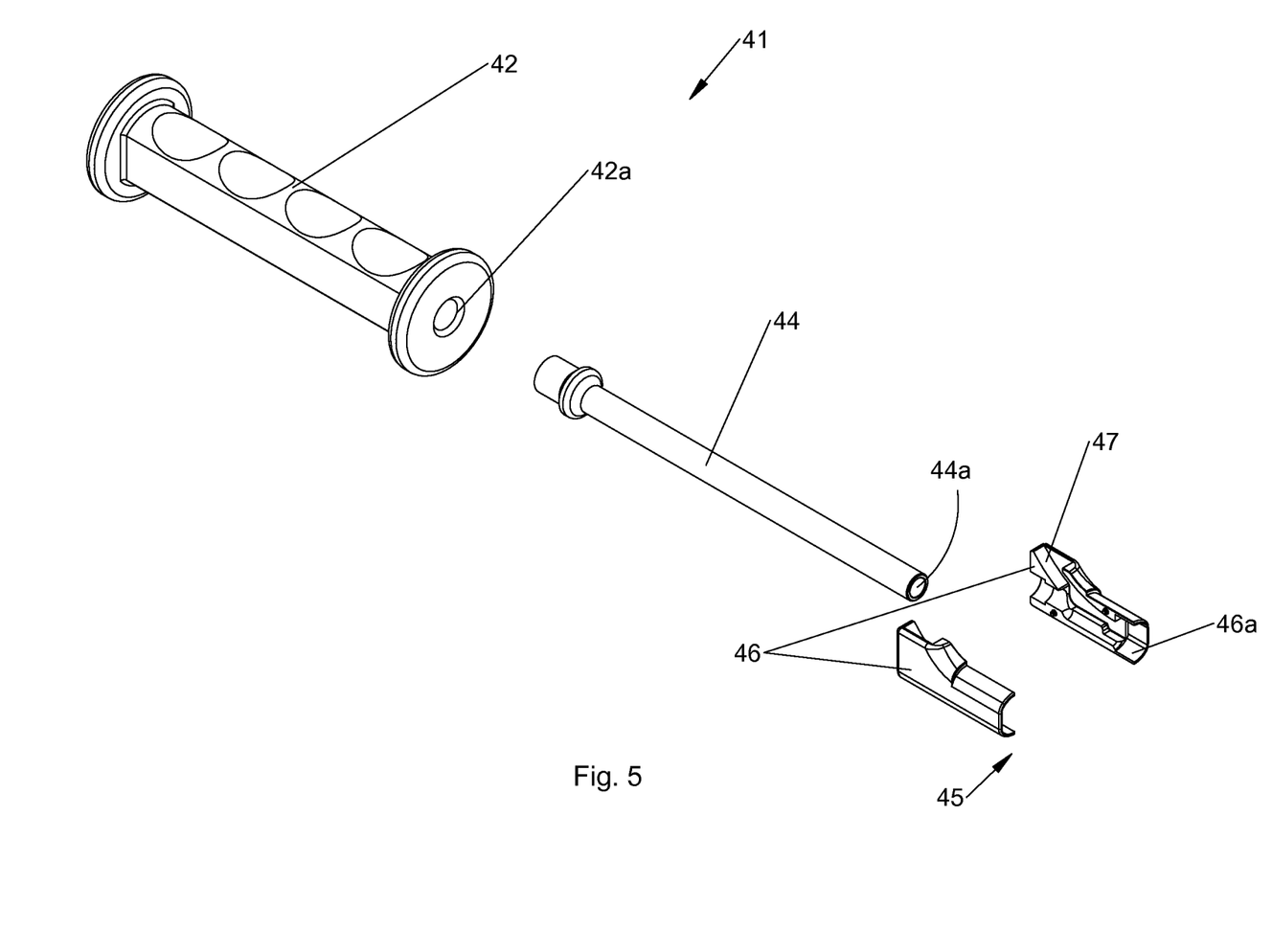
FIG. 5 is an exploded view of a drill guide assembly of the drilling apparatus of FIG. 4.
Figure 6:
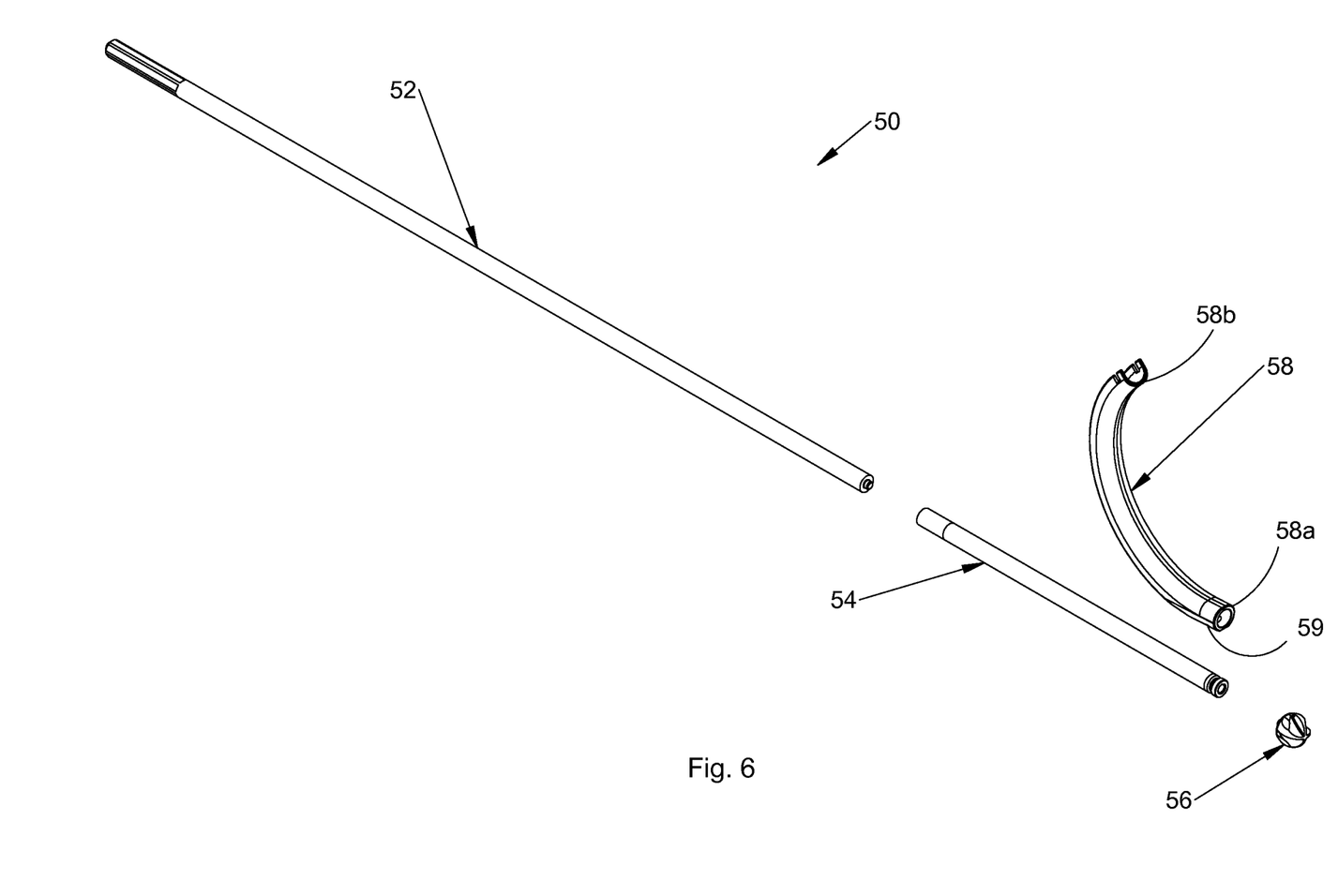
FIG. 6 is an exploded view of a drive shaft assembly of the drilling apparatus of FIG. 4 illustrating a flexible distal portion in a non-curved configuration.

Referring now to FIGS. 4-6, a drilling apparatus 40 may be used in accordance with the present disclosure to create the drilled hole 110 (FIG. 11) in bony elements. The drilling apparatus 40 includes a drill guide assembly 41 and a drill shaft assembly 50. The drill guide assembly 41 includes a handle 42, a guide shaft 44, and a distal section 45 formed from a pair of side guides 46. The handle 42 defines a first passage 42a about a longitudinal axis thereof. The handle 42 receives a proximal end of the guide shaft 44 within a distal end of the first passage 42a. The distal end of the handle 42 may be coupled to the proximal end of the guide shaft 44 by a variety of known techniques including, but not limited to, threaded engagement, a friction fit, a snap ring, an adhesive, welding, etc.

The guide shaft 44 defines a second passage 44a in communication with the first passage 42a. The side guides 46 couple together over the distal end of the guide shaft 44 to form the distal section 45. The distal section 45 defines a third passage 46a therethrough in communication with the second passage 44a. The first, second, and third passages 42a, 44a, 46a form a drill channel 43 (FIG. 4) through the drill guide assembly 41. The side guides 46 may be coupled together by a variety of known techniques including but not limited to a friction fit, screwing, gluing, welding, etc. The distal section 45 defines a guide slot 47 adjacent the proximal end thereof, adjacent the distal end of the guide shaft 44, and in communication with the third passage 46a. The guide slot 47 is configured to slidably receive the curved guide 58.

Figure 7:
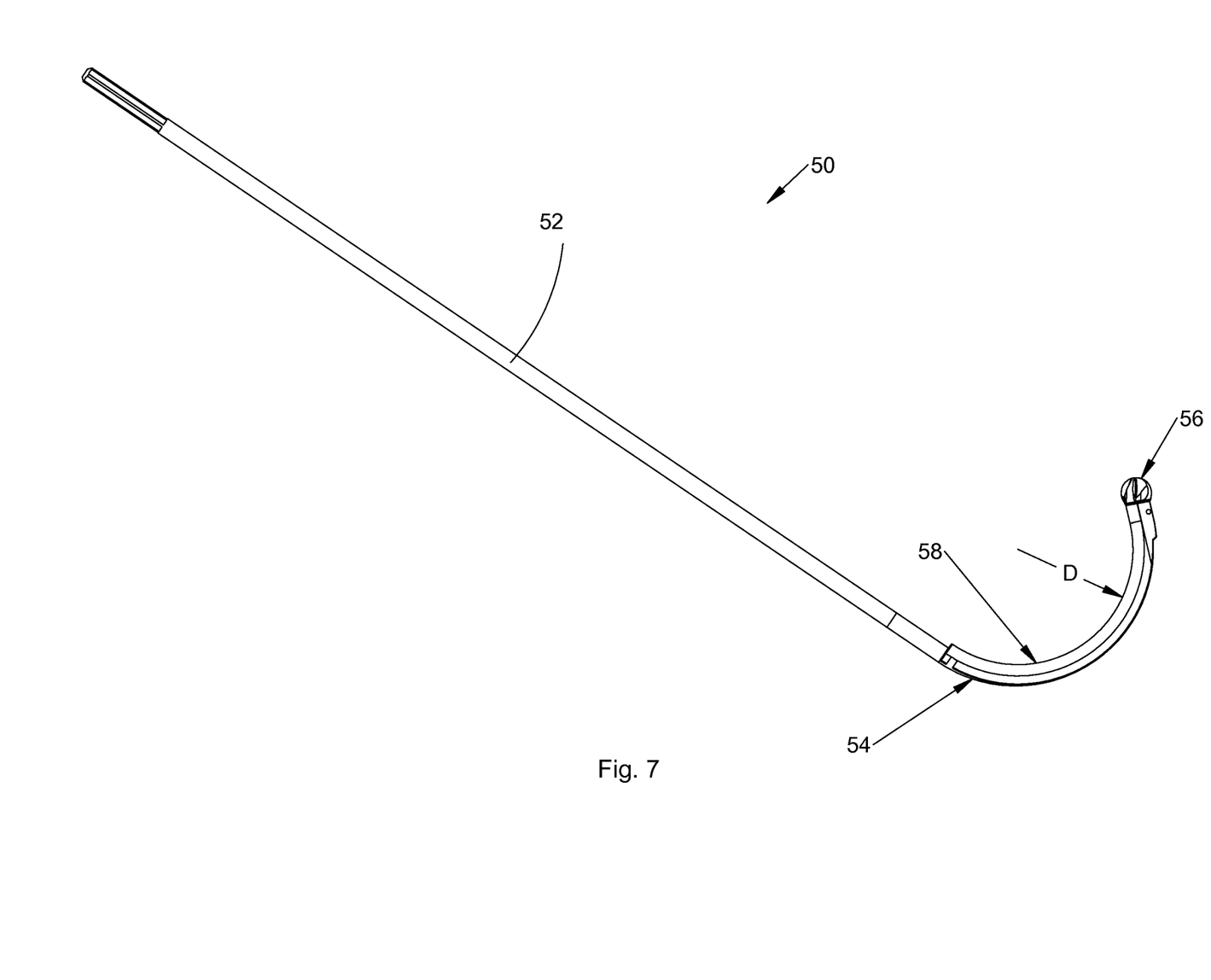
FIG. 7 is a view of the drive shaft assembly of FIG. 6 illustrating the flexible distal portion in a curved configuration.

Referring to FIGS. 6 and 7, the drill shaft assembly 50 includes a proximal portion 52, a flexible distal portion 54, a drill tip 56, and a curved guide 58. The proximal portion 52 may be rigid such that during use the proximal portion 52 remains in a substantially linear configuration. A proximal end of the flexible distal portion 54 is coupled to the distal end of the proximal portion 52. In some embodiments, the proximal and distal portions 52, 54 are integrally formed with one another to form a unitary construct. When non-stressed, the flexible distal portion 54 is in the non-curved or linear configuration as shown in FIG. 6. When a stress or force is applied to the flexible distal portion 54, the flexible distal portion 54 deflects to a curved configuration as shown in FIG. 7. In use, the flexible distal portion 54 rotates about its longitudinal axis in cooperation with rotation of the proximal portion 52 in either of the non-curved or curved configurations.

The drill tip 56 is coupled to the distal end of the flexible distal portion 54. The drill tip 56 may be coupled to the distal end of the flexible distal portion 54 by a variety of known techniques including, but not limited to, threaded engagement, friction fit, snap ring, welding, etc. The drill tip 56 is configured to create a hole through bone in contact therewith as the drill tip 56 is rotated. The drill tip 56 is configured for forward cutting and/or side cutting. In embodiments, the drill tip 56 is integrally formed on the distal end of the flexible distal portion 54. The drill tip 56 may be sized and configured to be partially or fully retracted into the third passage 46a of the drill guide assembly 40. In some embodiments, the drill tip 56 is sized to prevent the drill tip 56 from retracting into the second passage 44a.

With particular reference to FIG. 7, the curved guide 58 defines a radius of curvature D. The radius of curvature D may be constant along the entire length of the curved guide 58. However, it is also within the scope of this disclosure that the radius of curvature of the curved guide 58 varies along the length of the curved guide 58 (e.g., the radius of curvature of the curved guide 58 may increase or decrease along the length of the curved guide 58). In addition, the radius of curvature of the curved guide 58 may be similar to or the same as the radius of curvature C of the shank 16 (FIG. 3) to create a drilled hole (e.g., drilled hole 110 (FIG. 11) for the implant 10 as detailed below.

Referring to FIG. 6, a first end 58a of the curved guide 58 includes a coupling mechanism 59 configured to capture a portion of the flexible distal portion 54 and steer the flexible distal portion 54 as the flexible distal portion 54 advances. The coupling mechanism 59 permits the flexible distal portion 54 to rotate relative to the curved guide 58. The curved guide 58 may be substantially half-cylindrical in shape to substantially conform to the outer surface of the flexible distal portion 54. The curved guide 58 may be curved such that the outer wall has a smaller radius of curvature than the inner wall of the half-cylindrical shape as shown in FIGS. 6 and 7. The curved guide 58 is rigid such that the curved guide 58 maintains the radius of curvature D. A second end 58*b* of the curved guide 58 may include a stop that prevents the second end 58*b* from passing through the guide slot 47. It is also within the scope of this disclosure that the coupling mechanism 59 may prevent the first end 58*a* from passing through the guide slot 47. An example of a suitable drill shaft assembly is disclosed in U.S. Pat. Nos. 6,447,518 and 6,053,922 the contents of each is incorporated herein in its entirety Referring to FIGS. 3 and 8-11, the drilling apparatus 40 creates a drilled hole 110 in a bony element of an anatomy in accordance with the present disclosure. A curved guide (e.g., curved guide 58) with a predefined radius of curvature corresponding to the radius of curvature of a shank 16 of an implant 10 to be inserted into the bony element is selected. The first end 58*a* of the curved guide 58 is positioned within the guide slot 47 defined by the side guides 46 of the drill guide assembly 41. The side guides 46 are joined together to form the distal section 45 and to capture the curved guide 58 within the guide slot 47. The proximal and distal portions 52, 54 of the drill shaft assembly 50 are inserted through the drill channel 43 of the drill guide assembly 41 such that the distal end of the flexible distal portion 54 extends from the distal end of the distal section 45 and the proximal end of the proximal portion 52 extends from the proximal end of the handle 42 as shown in FIG. 3. The drill tip 56 may be removably coupled to the distal end of the flexible distal portion 54 and coupled to the flexible distal portion 54 through the coupling mechanism 59 to couple the flexible distal portion 54 to the curved guide 58.

Figure 8:
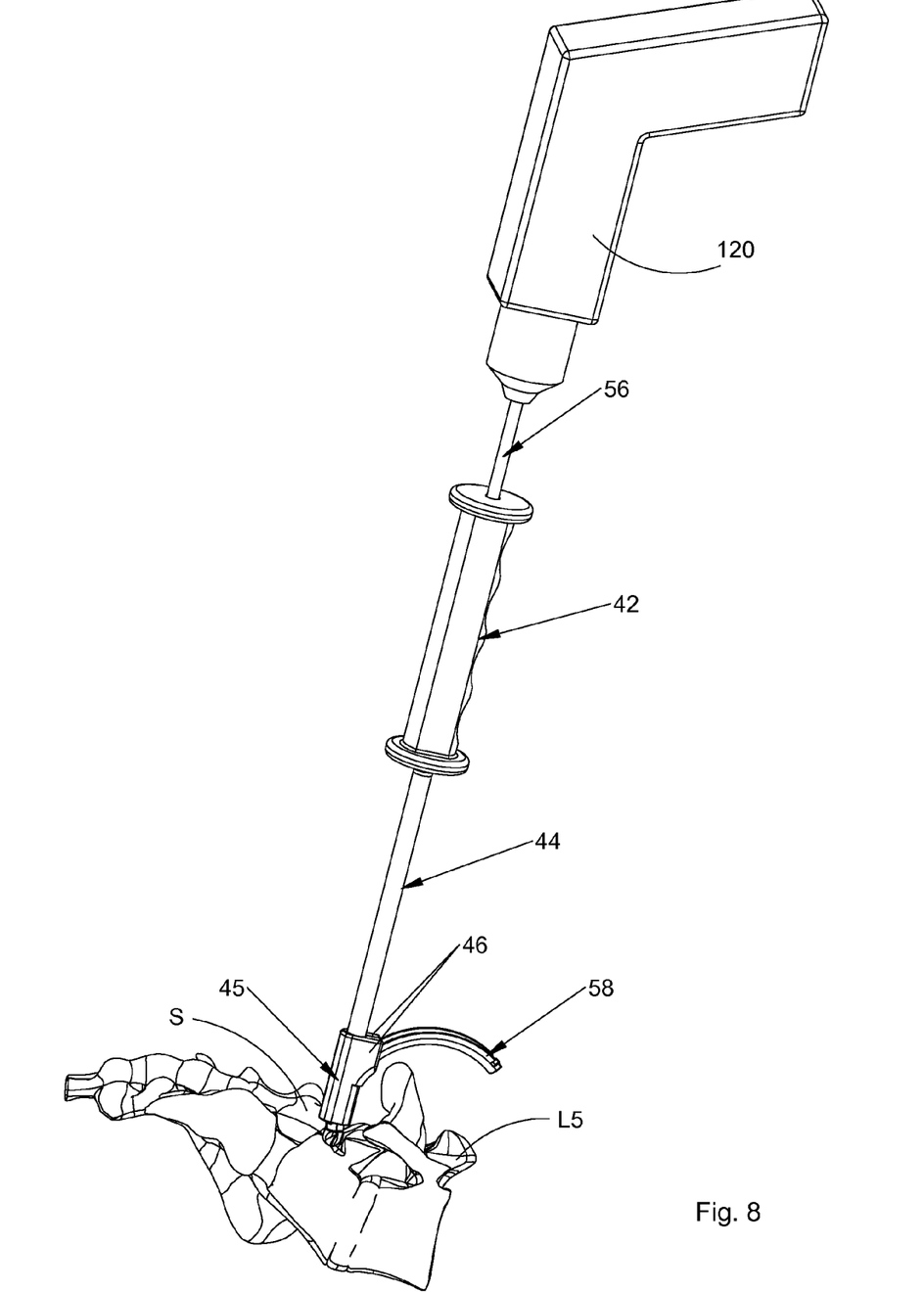
FIGS. 8-10 show a progression of side perspective views of the drilling apparatus of FIG. 4 and cutaway views of bony elements of an anatomy illustrating the drilling apparatus creating a drilled hole through the bony elements.

With particular reference to FIG. 8, the drill shaft assembly 50 is positioned such that the drill tip 56 abuts the bony element at a desired mounting point for a spinal rod (e.g., spinal rod 100 (FIG. 1) with the flexible distal portion 54 in the unstressed configuration. The drill tip 56 may be partially or wholly disposed within the third passage 46*a* of the drill guide assembly 41 and the distal end of the side guides 46 of the drill guide assembly 41 may be positioned against a bony element (e.g., sacrum S) in which the implant 10 is to be inserted. The distal end of the side guides 46 may be pinned or screwed in place against the bony element.

Figure 9:
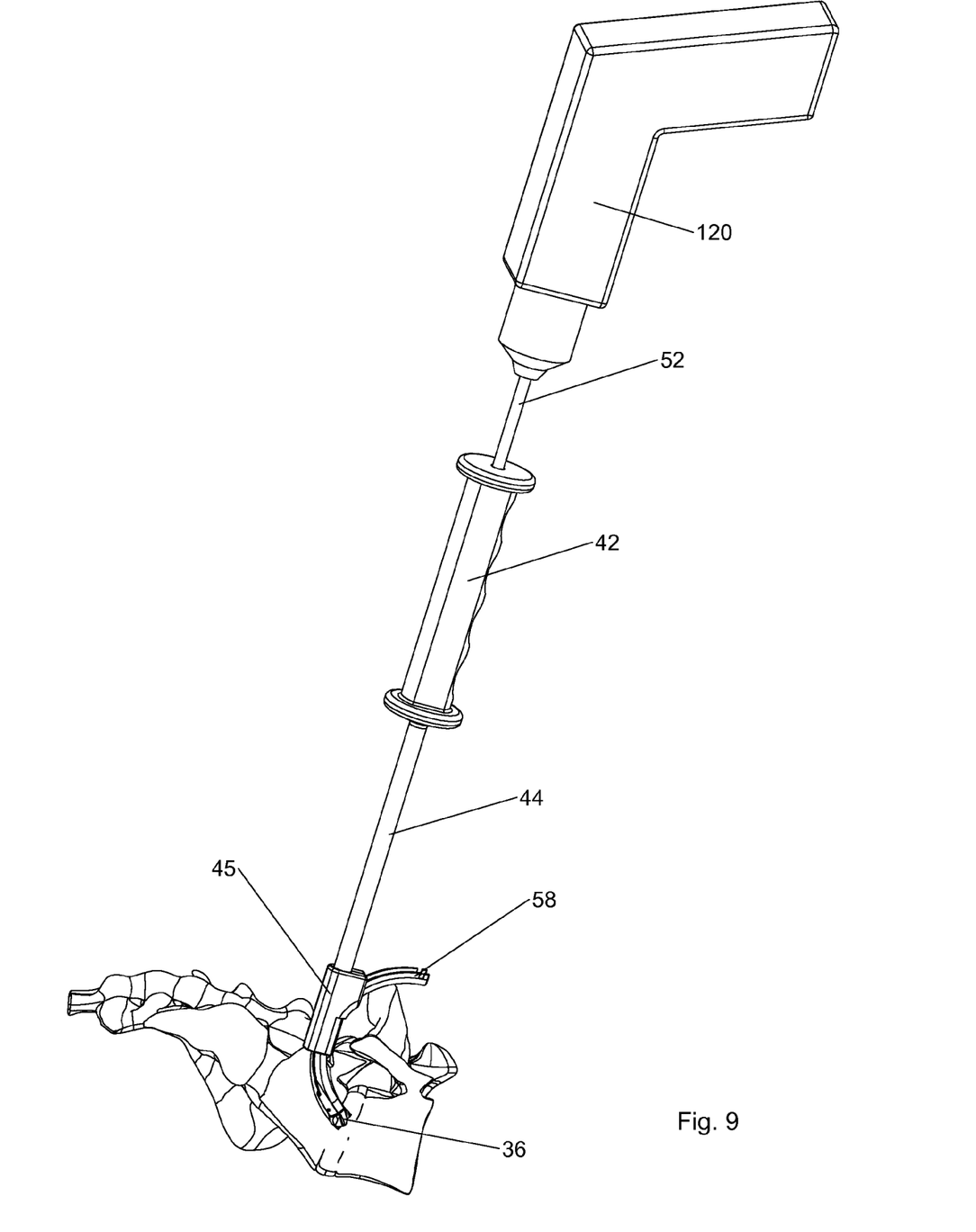
Figure 10:
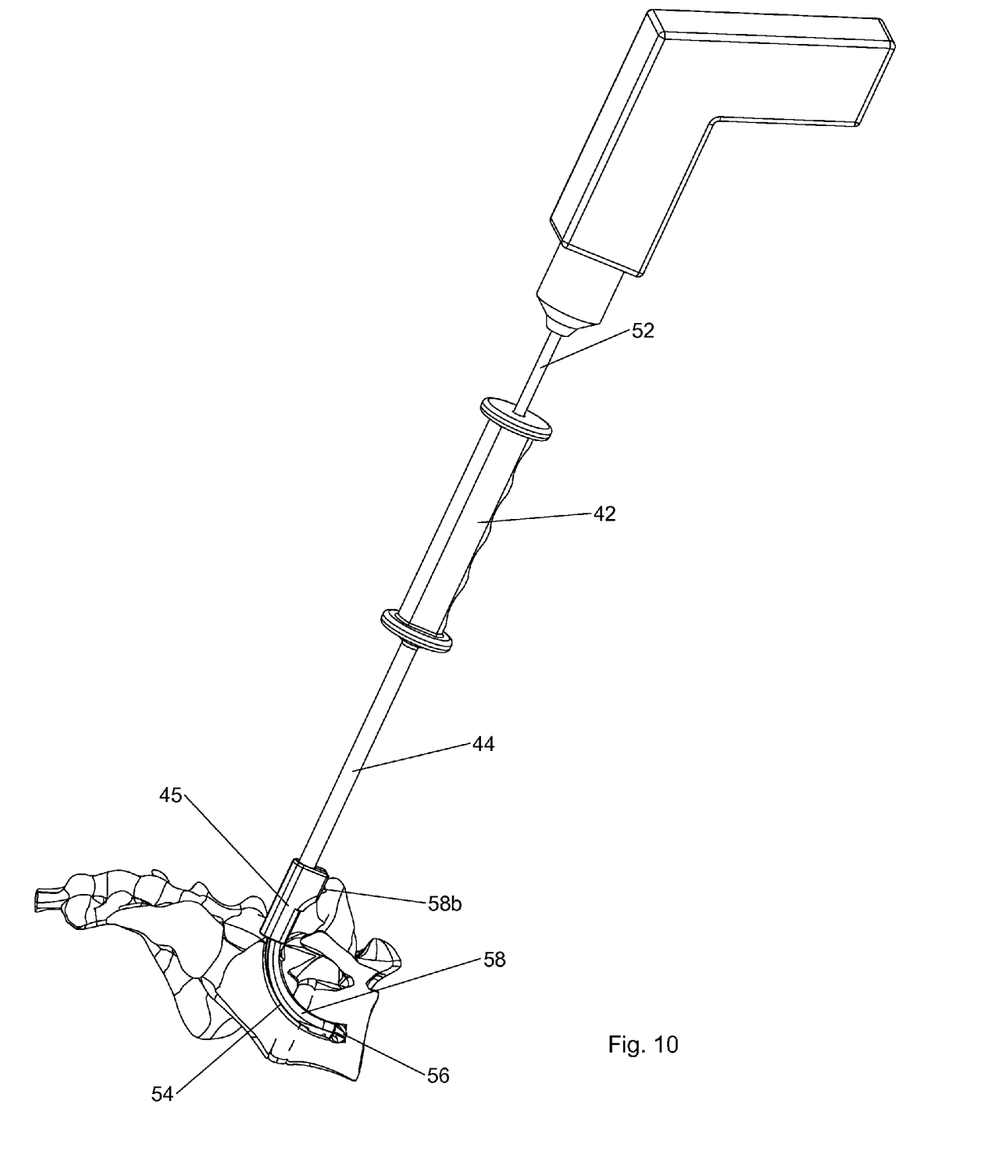

A drill 120 is coupled to the proximal end of the proximal portion 52 to rotate the proximal portion 52 about a longitudinal axis thereof as shown in FIG. 9. The drill 120 may be a powered instrument as shown or a manual handle. It will be appreciated that the flexible distal portion 54 and the distal tip 56 cooperate with the rotation of the proximal portion 52. As the proximal portion 52 is rotated, the flexible distal portion 54 is advanced through the side guides 46 and the drill tip 56 creates a hole through the bony element as shown in FIG. 9. As the flexible distal portion 54 advances, the curved guide 58 is advanced through the guide slot 47 and applies a force to the flexible distal portion 54 to steer the drill tip 56 along a predefined arcuate path defined by the radius of curvature D of the curved guide 58. As the curved guide 58 stresses the flexible distal portion 54, the flexible distal portion 54 deflects away from the longitudinal axis of the proximal portion 52 to follow the radius of curvature D of the curved guide 58. The drill tip 56 uses a side-cutting action to cooperate with the deflection of the flexible distal portion 54. The flexible distal portion 54 may be advanced until the stop adjacent the second end 58*b* of the curved guide 58 engages the guide slot 47 to prevent excessive advancement of the flexible distal portion 54 as shown in FIG. 10.

Figure 11:
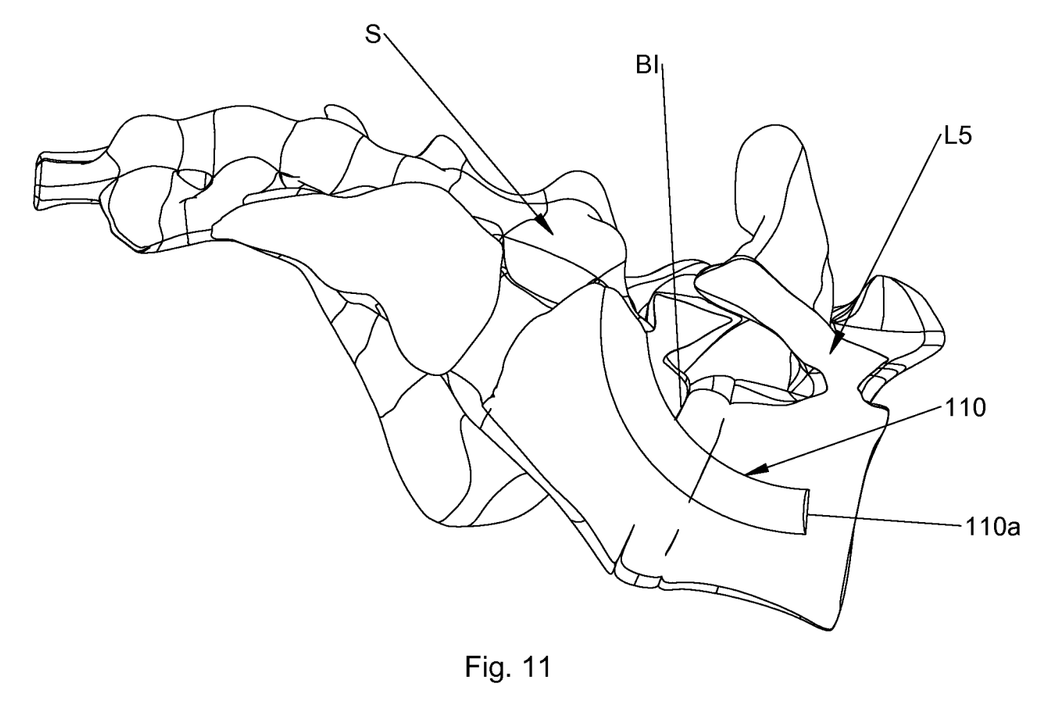
FIGS. 11-13 show a progression of cutaway views of the bony elements of the anatomy of FIG. 10 illustrating the insertion of the implant into the drilled hole and the securing of a spinal rod to the implant.

When the drill tip 56 reaches a desired depth, the drill tip 56 is withdrawn from the drilled hole 110 as shown in FIG. 11. When the drill tip 56 is withdrawn, the drilling apparatus 40 is removed from the bony element leaving a drilled hole 110 having a radius of curvature similar to the radius of curvature of the curved guide 58 and a depth substantially equal to the length between the first and second ends 58*a*, 58*b* (FIG. 6) of the curved guide 58. The drilled hole 110 may be defined within a single bony element (e.g., sacrum S). It is also within the scope of this disclosure that the drilled hole 110 may pass through more than one bony element; for example, the drilled hole 110 may pass through a first bony element (e.g., sacrum S), through a bone interface BI, and into a second bony element (e.g., vertebra L5).

Figure 12:
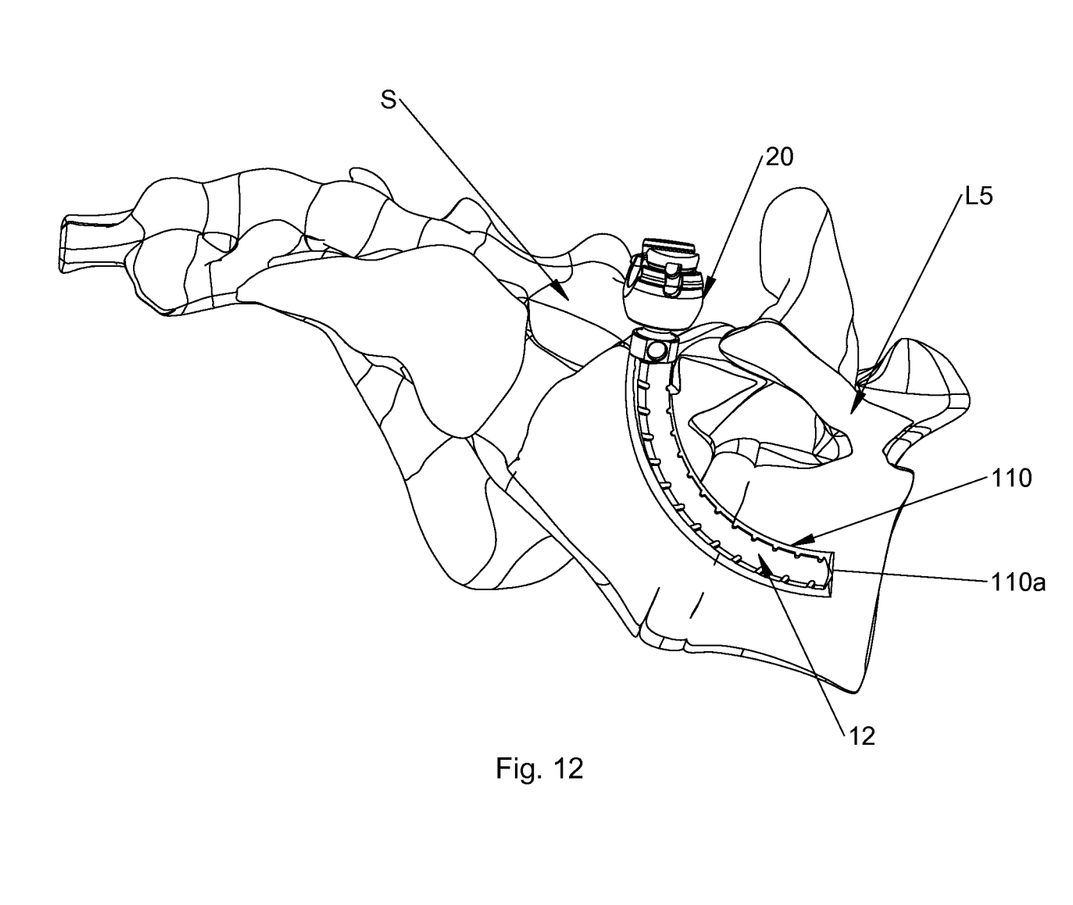
Figure 13:
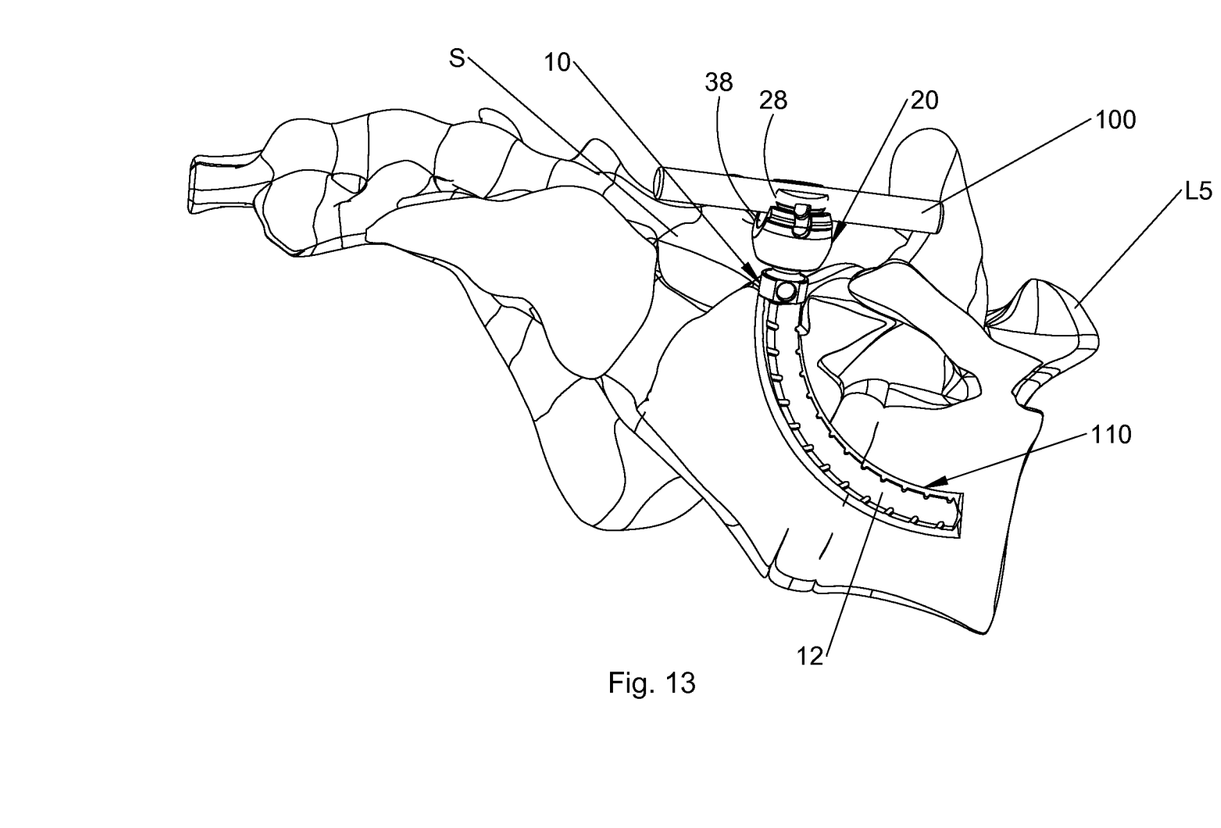

Referring now to FIGS. 11-13, the implant 10 is seated within the drilled hole 110 to fix the bony elements (e.g., sacrum S and vertebra L5) relative to one another and to provide a fixation point for a spinal rod (e.g., spinal rod 100). When the drilled hole 110 passes through more than one bony element, the implant 10 may fix the bony elements relative to one another such that the bony elements fuse to one another; continuing the example above, the sacrum S is fused to the vertebra L5.

To seat the implant 10 into the drilled hole 110, the shank 16 of the implant 10 is inserted into the drilled hole 110 until the shank 16 is fully seated within the drilled hole 110 as shown in FIG. 12 (i.e., the distal end of the shank 16 is adjacent a bottom 110*a* of the drilled hole 110). The diameter or shape of the shank 16 may partially interfere with the diameter or shape of the drilled hole 110 requiring an additional force to be applied to the implant 10 to insert the shank 16 into the drilled hole 110. A mallet (not shown) may be used to apply an additional force to the implant 10 to insert the implant 10 within the drilled hole 110. It will be appreciated that the partial interference of the diameter or shape of the shank 16 may secure the shank 16 within the drilled hole 110 and/or the first and second bony elements relative to one another. It will also be appreciated that the shank 16 is rigid to substantially maintain its shape as additional force is applied to seat the shank 16 into the drilled hole 110.

When the shank 16 is fully seated within the drilled hole 110, the housing 20 is oriented to receive the spinal rod 100 as shown in FIG. 13 (i.e., the housing 20 is orientated such that the saddles 28, 38 align with the spinal rod 100). The spinal rod 100 is then secured within the housing as detailed above. The spinal rod 100 may be secured to a plurality of implants 110.

It will be appreciated that the outer surface of the shank 16 may be textured or patterned to prevent the shank 16 from backing out of the drilled hole 110 or to enhance bone growth to secure the shank 16 within the drilled hole 110. The recesses 17 may also engage the sides of the drilled hole 110 to prevent the shank 16 from backing out of the drilled hole 110 or to enhance bone growth to the shank 16.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An implant comprising:
   an implantable portion including a head and a shank extending from the head, the shank defining a radius of curvature, the shank having a solid outer surface, the shank configured to be disposed within first and second bony elements to maintain the first and second bony elements relative to one another in a fixed orientation; and
   a housing pivotally and rotatably coupled to the head, the housing configured to secure a rod to the implantable portion, the housing fixed relative to the implantable portion when the rod is secured to the implantable portion.

2. The implant of claim 1, wherein housing is a taper lock housing.

3. The implant of claim 1, wherein the housing is a set screw housing.

4. The implant of claim 1, wherein the shank defines a plurality of recesses in the outer surface thereof.

5. The implant of claim 1, wherein the shank is generally cylindrical.

6. The implant of claim 1, wherein the implantable portion is configured for insertion through a sacrum of a patient and into an L5 vertebra of the patient to create a fusion of the sacrum and the L5 vertebra.

7. The implant of claim 1, wherein the head and the shank are integrally formed with one another.

8. The implant of claim 1, wherein the shank is a solid shaft.

9. The implant of claim 1, wherein the outer surface of the shank is uninterrupted.

10. A system for inserting an implant in bony anatomy of a patient, the system comprising:
    a drilling apparatus for creating a curved drilled hole that passes through a first bony element and into a second bony element, the drilling apparatus including:
        a drill guide assembly including a guide shaft and a distal section, the guide shaft defining a drill channel and the distal section defining a guide slot in communication with the drill channel; and
        a drill shaft assembly including a proximal portion, a flexible distal portion, and a curved guide, the proximal and flexible distal portions slidably and rotatably disposed within the drill channel, the curved guide coupled to the flexible distal portion and slidably disposed within the guide slot, the curved guide deflecting the flexible distal portion as the drill shaft assembly advances through the drill guide assembly such that the flexible distal portion defines a curved path; and
    an implant including:
        an implantable portion including a head and a shank extending from the head, the shank defining a radius of curvature, the shank having a solid outer surface, the shank configured to be positioned within the curved drilled hole that passes through the first bony element and into the second bony element such that the first and second bony elements are secured relative to one another to promote fusion therebetween, the shank being rigid along its entire length; and
        a housing pivotally and rotatably coupled to the head, the housing configured to secure a rod to the implantable portion, the housing fixed relative to the implantable portion when the rod is secured to the implantable portion.

11. The system of claim 10, wherein the drill shaft assembly includes a drill tip coupled to a distal end of the flexible distal portion, the drill tip configured to forward cut and side cut bone in contact therewith.

12. The system of claim 10, wherein the curved guide includes a coupling mechanism adjacent a first end thereof, the coupling mechanism capturing the flexible distal portion while permitting the flexible distal portion to rotate relative to the curved guide.

13. The system of claim 12, wherein the coupling mechanism prevents the first end of the curved guide from sliding through the guide slot.

14. The system of claim 10, wherein the curved guide includes a stop adjacent a second end thereof, the stop preventing the second end of the curved guide from sliding through the guide slot.

15. The system of claim 10, wherein the shank defines a plurality of recesses in the outer surface thereof.

16. The system of claim 15, wherein the shank is a solid shaft.

17. An implant comprising:
    an implantable portion including a head and a shank extending from the head, the shank defining a radius of curvature, the shank having a solid outer surface defining a plurality of recesses, the shank configured to secure first and second bony elements relative to one another such that the first and second bony elements fuse to one another, the shank is configured to be disposed within each of the first and second bony elements; and
    a housing pivotally and rotatably coupled to the head, the housing configured to secure a rod to the implantable portion, the housing fixed relative to the implantable portion when the rod is secured to the implantable portion.

18. The system of claim 17, wherein the shank is a solid shaft.

19. The system of claim 17, wherein the head and the shank are integrally formed with one another.

20. The system of claim 17, wherein housing is a taper lock housing.

21. The system of claim 17, wherein the housing is a set screw housing.

22. The system of claim 17, wherein the implantable portion is configured for insertion through a sacrum of a patient and into an L5 vertebra of the patient to create a fusion of the sacrum and the L5 vertebra.

* * * * *